United States Patent
Fujimoto

(10) Patent No.: US 6,794,193 B2
(45) Date of Patent: Sep. 21, 2004

(54) METHOD OF ASSAYING A SPECIMEN USING A REAGENT

(75) Inventor: Koji Fujimoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/848,330

(22) Filed: May 4, 2001

(65) Prior Publication Data

US 2001/0053515 A1 Dec. 20, 2001

(30) Foreign Application Priority Data

May 8, 2000 (JP) ..................................... P.2000-134478

(51) Int. Cl.[7] .......................... G01N 35/00; G01N 35/10
(52) U.S. Cl. .......................... 436/49; 436/179; 436/180
(58) Field of Search .......................... 436/49, 179, 180; 73/864.11, 864.12

(56) References Cited

U.S. PATENT DOCUMENTS 4,633,413 A * 12/1986 Caveney et al. ............ 700/265

FOREIGN PATENT DOCUMENTS

| EP | 0 843 176 A1 | 5/1998 |
| EP | 0 884 104 A1 | 12/1998 |
| JP | 08122336 | 5/1996 |

* cited by examiner

*Primary Examiner*—Jan M. Ludlow
(74) *Attorney, Agent, or Firm*—Sughrue Mion, PLLC

(57) ABSTRACT

A method of assaying a specimen, comprising: preparing (i) a specimen, (ii) a liquid cell in which a liquid used for assaying a component in the specimen, such as a liquid reagent or a liquid diluent, is to be contained, and (iii) a mixing cell wherein the specimen and the liquid are mixed; supplying a liquid reagent into the liquid cell in an amount exceeding the amount required in the assay; pipetting a portion of the specimen and a portion of the liquid into the mixing cell using a pipetting tip; and washing the pipetting tip with the liquid remaining in the liquid cell.

23 Claims, 1 Drawing Sheet

METHOD OF ASSAYING A SPECIMEN USING A REAGENT

BACKGROUND OF THE INVENTION

1. Filed of the Invention

The present invention relates to a method wherein a specimen, such as blood, is pipetted into a mixing cell and is allowed to react with a reagent to thereby analyze a component thereof.

2. Discussion of the Background Art

Operations for pipetting specimens and reagents into reactors have been mechanized in order to prevent scatter from worker to worker, to save personnel expenses, to shorten the assay time, etc. Since these pipetting apparatuses are very expensive, it has been typical practice to employ a single apparatus for plural purposes even when plural types of reagents are employed.

To simplify such a pipetting apparatus, and to avoid contamination of reagents with each other, JP-A-8-122336 (the term "JP-A" as used herein means an "unexamined published Japanese patent application") discloses an assay method wherein a pipetting tip (which is called a pipette in this document) is employed with the use of a cartridge provided with a well for optical measurement (hereinafter referred to as a "measurement cell"), a holding member for holding the pipetting tip and another well in which a washing liquor is to be contained (hereinafter referred to as a "washing liquor cell").

The above-described cartridge is employed when a specimen (blood, body fluid, etc.) is pipetted into the mixing cell in a definite amount either directly or after diluting with a liquid diluent contained in the dilution cell, and a reagent contained in the liquid reagent cell is collected in a definite amount and is discharged into the above-described mixing cell to which the specimen has been already added, thereby initiating the assay.

In the cartridge as described above, a single pipette is used in all of the operations of pipetting and diluting the specimen, pipetting the liquid reagent, pipetting the washing liquor, etc. Although these pipetting operations are carried out by using a single pipette, there arises no contamination. This is because the pipetting tip is washed with the washing liquor preliminarily supplied into the washing liquor cell. This washing liquor cell also serves as a waste liquor cell containing the waste liquor after washing. So long as there arises no trouble of contamination, it is advantageous to carry out all of these pipetting operations with the use of a single pipette. These advantage arise because it is unnecessary in this apparatus to exchange pipetting tips frequently, or to provide a member for washing the tip, as in the conventional cases and, thus, the assay apparatus size can be reduced.

As in the assay method disclosed by JP-A-8-122336 described above, it has been a common practice that a pipetting tip contained in a cartridge is set to a nozzle immediately after the initiation of the assay and the first specimen, liquid reagent or the like is sucked thereby. In most cases, the first specimen, liquid reagent, or the like, is sucked without effecting any pretreatment. Typically, the inside of the pipetting tip is treated with silicone, etc. to thereby discharge all of the collected liquid. When a liquid having a low viscosity is collected, the liquid can be sufficiently discharged from the pipetting tip without remaining therein and, thus, the liquid collection can be performed at a high accuracy.

However, the cartridge disclosed in JP-A-8-12233 must be provided with exclusive washing liquor cells for containing washing liquor for washing the pipetting tip. Since insufficient washing causes contamination, the washing should be carried out at least to such an extent that avoids contamination. Therefore, a plural number of washing liquor cells are necessary. As a result, the cartridge is enlarged and the performance is worsened.

As described above, it is unavoidable to use a new pipetting tip immediately after the initiation of the assay. When a highly viscous liquid (such as whole blood, etc.) is sucked, the volume of the sucked specimen varies even though the interior of the pipetting tip has been treated with silicone as described above. As a result, there arise errors in the assay data. This is apparently because whole blood has both of hydrophilic and hydrophobic natures, but the pipetting tip exhibits a highly hydrophobic nature that brings about strong resistance in the course of sucking. The viscosity might also affect this phenomenon.

SUMMARY OF THE INVENTION

An object of the present invention is to provide an assay method whereby a tip can be washed without providing any cell exclusively for washing.

Another object of the present invention is to provide an assay method whereby a liquid can be accurately collected in a definite amount by using a pipetting tip.

These and other objects of the present invention has been achieved by a method of assaying a specimen, comprising:
preparing (i) a specimen, (ii) a liquid cell in which a liquid used for assaying a component in the specimen is to be contained, and (iii) a mixing cell wherein the specimen and the liquid are mixed;
supplying a liquid reagent into the liquid reagent cell in an amount exceeding the amount required in the assay;
pipetting a portion of the specimen and a portion of the liquid into the mixing cell using a pipetting tip; and
washing the pipetting tip with the liquid remaining in the liquid cell.

Moreover, these and other objects of the present invention has been achieved by a method of assaying a specimen, comprising:
preparing (i) a specimen, (ii) a liquid reagent cell in which a liquid reagent is to be contained and a liquid diluent in which a liquid diluent is to be contained, and (iii) a mixing cell wherein the specimen and the liquid reagent are mixed;
supplying a liquid reagent and a liquid diluent respectively into the liquid reagent cell and the liquid diluent in respective amounts each exceeding the amount required in the assay; and
pipetting a portion of the specimen, a portion of the liquid reagent and a portion of the liquid diluent into the mixing cell using a pipetting tip; and
the method further comprising at least one step of:
washing the pipetting tip with the liquid remaining in the liquid reagent cell, and
washing the pipetting tip with the liquid remaining in the liquid diluent cell.

DETAILED DESCRIPTION OF THE INVENTION

Figure 1:
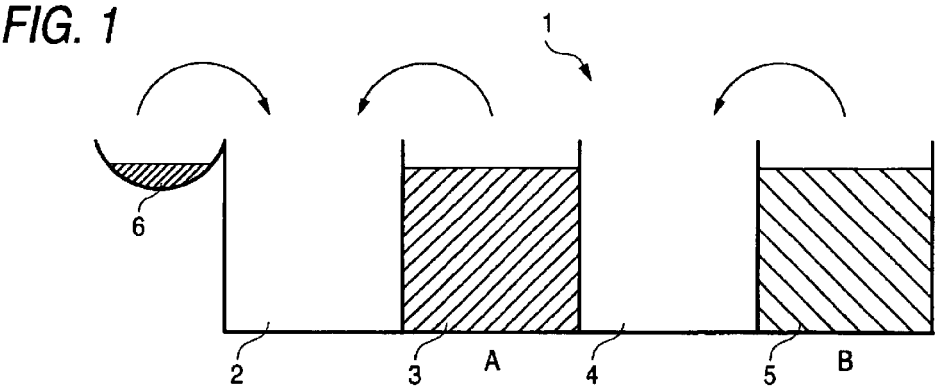
FIG. 1 is a sectional view of a cartridge, and illustrates the early stage of the assay method of Example 1.

In the method of the present invention, the liquid used for assaying a component in the specimen is preferably at least one selected from the group consisting of a liquid reagent and a liquid diluent (e.g., water, physiologic saline, buffer, organic solvent, etc.).

For example, the step of washing the pipetting tip with the liquid remaining in the liquid cell is preferably performed after the step of pipetting a portion of the liquid or a portion of the specimen into the mixing cell.

Specifically, the method of the present invention using the liquid used for assaying a component of in the specimen is more preferably performed by the order of (I) or (II):

(I) the step of pipetting and a portion of the liquid into the mixing cell using a pipetting tip, and then
the step of pipetting a portion of the specimen into the mixing cell using a pipetting tip, and then
the step of washing the pipetting tip with the liquid remaining in the liquid cell; or (II) the step of pipetting and a portion of the specimen into the mixing cell using a pipetting tip, and then
the step of pipetting a portion of the liquid into the mixing cell using a pipetting tip, and then
the step of washing the pipetting tip with the liquid remaining in the liquid cell.

According to this assay method, the pipetting tip is washed with the liquid used for assaying a component in the specimen, such as the liquid reagent and/or the liquid diluent, supplied in an amount exceeding the amount required in the assay. Therefore, it is unnecessary to prepare any washing liquor separately. Moreover, the pipetting tip can be washed in the liquid reagent cell and/or the liquid diluent cell after pipetting the liquid reagent and/or liquid diluent or the specimen in an amount required in the assay. Therefore, it is also unnecessary to prepare any separate washing tank or separate waste liquor tank.

Specifically, the step of washing the pipetting tip with the liquid remaining in the liquid reagent cell is preferably performed after the step of pipetting a portion of the liquid reagent, a portion of the liquid diluent or a portion of the specimen into the mixing cell.

Also, the step of washing the pipetting tip with the liquid remaining in the liquid diluent cell is preferably performed after the step of pipetting a portion of the liquid reagent, a portion of the liquid diluent or a portion of the specimen into the mixing cell.

More specifically, the method of the present invention using the liquid reagent and the liquid diluent is preferably performed by any one of the orders of (I) to (IV):

(I) the step of pipetting and a portion of the liquid diluent into the mixing cell using a pipetting tip, and then
the step of pipetting a portion of the specimen into the mixing cell using a pipetting tip, and then
the step of washing the pipetting tip with the liquid remaining in the liquid diluent cell, and then
the step of pipetting and a portion of the liquid reagent into the mixing cell using a pipetting tip;

(II) the step of pipetting and a portion of the liquid reagent into the mixing cell using a pipetting tip, and then
the step of pipetting a portion of the specimen into the mixing cell using a pipetting tip, and then
the step of washing the pipetting tip with the liquid remaining in the liquid reagent cell, and then
the step of pipetting and a portion of the liquid diluent into the mixing cell using a pipetting tip;

(III) the step of pipetting and a portion of the liquid reagent and a portion of the liquid diluent into the mixing cell using a pipetting tip, and then
the step of pipetting a portion of the specimen into the mixing cell using a pipetting tip, and then
the step of washing the pipetting tip with the liquid remaining in the liquid reagent cell;

(IV) the step of pipetting and a portion of the liquid reagent and a portion of the liquid diluent into the mixing cell using a pipetting tip, and then
the step of pipetting a portion of the specimen into the mixing cell using a pipetting tip, and then
the step of washing the pipetting tip with the liquid remaining in the liquid diluent cell.

The specimen may be diluted with the liquid diluent in the mixing cell or may be pipetted as a diluted specimen after diluted with the liquid diluent in another cell.

When, after washing, the waste liquor is not returned to the collection cell, but is discharged into another cell which does not participate in the assay, washing can be repeated so long as there remains the liquid reagent or the liquid diluent.

When the amount of the liquid reagent or the liquid diluent remaining in the cell is smaller than the amount required in a single washing operation, the whole remaining liquid is sucked and then the liquid diluent or the liquid reagent remaining in another cell is added for compensation, thereby carrying out the washing operation. Thus, arbitrary cell(s) may be provided, if necessary, without using any cell exclusively for the waste liquor. The arbitrary cell(s) thus provided may contain waste liquor obtained by plural washing operations.

A solid reagent can also be used in the mixing cell so long as the solid reagent is dissolved by the specimen or the liquid used for assaying the specimen, such as a liquid diluent. The term "liquid reagent" includes such a reagent that the solid reagent is dissolved in liquid.

In the assay method according to the present invention, the inside of the pipetting tip is preferably pre-washed with the liquid contained in the liquid reagent cell and/or the liquid diluent cell.

By moistening a new tip with the liquid reagent or the liquid diluent, the specimen or liquid reagent to be sucked next time can be accurately collected. Thus, it becomes possible to minimize the difference in pipetted volume between a highly viscous whole blood specimen and a less viscous plasma or serum specimen.

By moistening a new tip, it is expected that not only the specimen or liquid reagent to be sucked next time can be accurately collected, but also a favorable washing effect can be achieved in the subsequent step of washing the pipetting tip. This is apparently because the surface inside the pipetting tip (e.g., silicone surface) is coated with the pre-washing liquor.

In the step of pipetting into the mixing cell, a step of sucking and discharging the liquid in the mixing cell is preferably performed.

According to the present invention, a pipetting tip can be used repeatedly, which makes it possible to save resources and to reduce cost. Since it is unnecessary to provide a cartridge with washing liquors, washing liquor cells, or waste liquor cells, the cartridge per se can be small-sized. Moreover, a highly viscous specimen, such as whole blood, can be pipetted accurately. Thus, assay data with little error can be obtained, which is greatly advantageous in the field of clinical medicine.

The present invention is explained below based on Examples, but the present invention is not limited thereto.

EXAMPLE 1

An embodiment of the washing method with the pipetting tip according to the present invention will now be described with reference to the attached drawings.

FIG. 1 is a sectional view of a four-cell cartridge having 4 cells to be used in pipetting, which cells are connected to each other in series. The cartridge also includes a specimen container.

As cartridge 1, it is possible to use one made of, for example, a plastic (polystyrene resin, acrylic resin, vinyl chloride resin, etc.) or glass. It is preferred to use a cartridge made of polystyrene resin which is less expensive, and which is excellent in light-permeability and convenience in handling.

Cartridge 1 is provided with first mixing cell 2, first liquid reagent cell 3, second mixing cell 4, and second liquid reagent cell 5, from left to right. These cells are connected successively to each other because they are integrally molded. First liquid reagent cell 3 and second liquid reagent cell 5 contain liquid reagent A and another liquid reagent B, respectively, each in an amount exceeding the amount required in the assay. Sample container 6 located near cartridge 1, contains a specimen in an amount exceeding the amount required in assaying plural items.

Each cell (chamber, container, tank etc.) is sealed so as to prevent the liquid contained therein from leakage during transportation. The seal can be made of an aluminum foil or various polymer films either used alone or as a laminate. The cell may be opened by hand before use. Alternatively, the seal may be removed during use, for example, by a breaker.

As a pipetting tip, it is possible to use one made of, for example, a plastic (polystyrene resin, acrylic resin, vinyl chloride resin, etc.) or glass, and it is preferred that the inside thereof is coated with silicone.

To initiate the assay, a new pipetting tip is first set to a nozzle. After sucking and discharging liquid reagent A contained in first liquid reagent cell 3 with the pipetting tip, liquid reagent A is sucked in an amount required in the assay, and is then discharged into first mixing cell 2. Next, liquid reagent B is sucked in an amount required in the assay from second liquid reagent cell 5, and then is discharged into second mixing cell 4. The order of sucking and discharging liquid reagents A and B is selected so as to have no influence on the subsequent reactions with the specimen.

Figure 2:
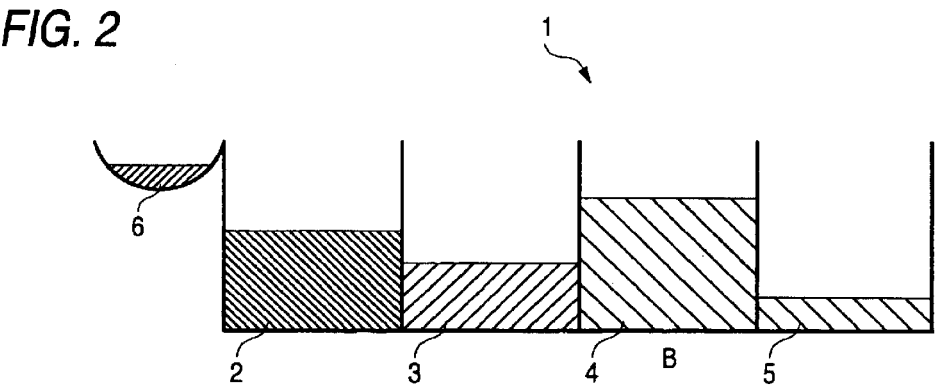
FIG. 2 is a sectional view of a cartridge, and illustrates an intermediate stage of the assay method of Example 1.

Subsequently, the specimen is sucked in an amount required in the assay from specimen container 6 and is discharged into first mixing cell 2. In this step, as shown in FIG. 2, first mixing cell 2 and second mixing cell 4 in cartridge 1 serve respectively as the mixing tanks of liquid reagent A and liquid reagent B, while first liquid reagent cell 3 and second liquid reagent cell 5 serve as washing tanks. Then, the liquid reagent is allowed to react with the specimen under stirring by repeating suction and discharge with the pipetting tip several times. Then, liquid reagent B remaining in liquid reagent cell 5 is sucked and discharged repeatedly by the pipetting tip to thereby wash the pipetting tip. After washing, the specimen is sucked in an amount required in the assay by the pipetting tip from specimen container 6, and is discharged into second mixing cell 4. Then, the liquid reagent is allowed to react with the specimen under stirring by repeating suction and discharge with the pipetting tip several times.

After the passage of a definite period of time seemingly ensuring the completion of the reaction, a change in the color or turbidity of the liquid reagent in association with the reaction is optically detected and, thus, the concentration of a specific component in the specimen is output.

By pre-contacting the new pipetting tip with liquid reagent B, it is expected that liquid reagent B can be accurately collected and the washing of the pipetting tip becomes further effective. Liquid reagent B used in washing is the liquid remaining in second liquid reagent cell 5 and, therefore, the same as the liquid reaction mixture in second mixing cell 4. Thus, there is no fear that the reaction is affected thereby.

EXAMPLE 2

In this experiment, a comparison was made between a case where whole blood was collected by using a new pipetting tip and another case where whole blood was collected after pre-washing a pipetting tip with a liquid reagent or a liquid diluent to thereby confirm whether or not the whole blood could be accurately collected.

In this Example, a 0.5% saponin solution in physiological saline was used as the liquid for diluting the specimen. First, a pipetting tip was set to a nozzle and 10 μl of whole blood was sucked immediately without pre-washing. Then, the whole blood contained in the pipetting tip was discharged and weighed. Next, another new pipetting tip was set to the nozzle which was then pre-washed by sucking and discharging the 0.5% saponin solution in physiological saline. Subsequently, 10 μl of whole blood was sucked and the whole blood contained in the pipetting tip was discharged and weighed with an electron balance. Table 1 shows the results.

TABLE 1

|   | Not pre-washed (g) | Pre-washed (g) |
|---|---|---|
| 1 | 0.0086 | 0.0099 |
| 2 | 0.0083 | 0.0104 |
| 3 | 0.0085 | 0.0106 |
| 4 | 0.0085 | 0.0107 |
| 5 | 0.0085 | 0.0106 |
| Average | 0.0085 | 0.0104 |

As the above table shows, an obvious difference is observed between the case of the collection with the new pipetting tip and the case with pre-washing with the 0.5% saponin solution in physiological saline.

Since the blood has a specific gravity of 1.07, the true weight of 10 μl of the whole blood amounts to 0.0107. Namely, the data in the case with pre-washing are closely similar to the true value, though some scatter is observed.

On the other hand, the data in the case with no pre-washing are far from the true value. Thus, the whole blood can be accurately collected by pre-washing the inside of the pipetting tip.

EXAMPLE 3

Next, a cartridge for diluting a specimen with a liquid diluent will be illustrated.

Figure 3:
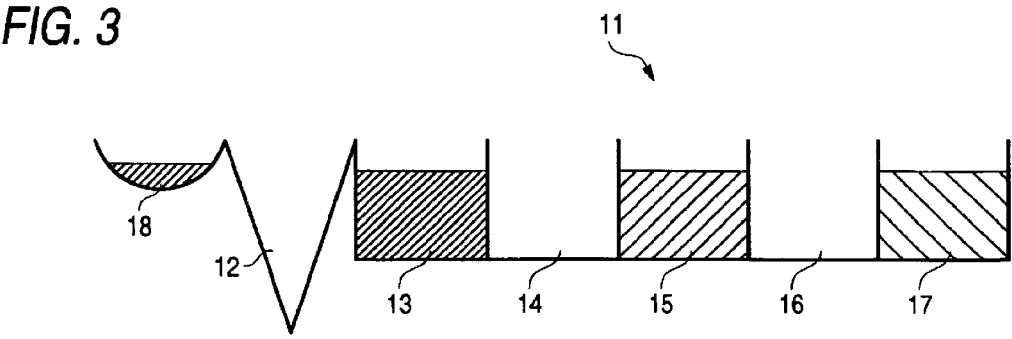
FIG. 3 is a sectional view of a cartridge, and illustrates the early stage of the assay method of Example 3.

As shown by the sectional view in FIG. 3, cartridge 11, which is made of a transparent plastic or the like as in Example 1, is provided with pipetting-tip-containing cell 12, liquid diluent cell 13, first mixing cell 14, first liquid reagent cell 15, second mixing cell 16, and second liquid reagent cell 17, from left to right. These cells are connected to each other because they are integrally molded. Liquid diluent cell 13 contains a liquid diluent for diluting a specimen in an amount exceeding the amount required in the assay.

Similarly, first liquid reagent cell 15 and second liquid reagent cell 17 contain liquid reagent A and another liquid reagent B, respectively, each in an amount exceeding the amount required in the assay. Specimen container 18, located near cartridge 11, contains whole blood, serum, or plasma, as a specimen to be assayed.

The assay is carried out in practice as follows. First, the pipetting tip in pipetting-tip-containing cell 12 is set to a nozzle. Then, the liquid for diluting the specimen in liquid diluent cell 13 is sucked and discharged to thereby pre-contact the pipetting tip. Next, the same liquid diluent is sucked in a required amount and is then discharged into first mixing cell 14. Furthermore, the same liquid diluent is sucked in a required amount and then discharged into second mixing cell 16. Since the rate of diluting the specimen varies from assay item to assay item, the amounts of the liquid diluent and the specimen vary depending on the item.

Specimen container 18 may contain various specimens. When whole blood is contained therein, it is separated into a blood cell layer and a plasma layer due to the passage of time after collection. Then, the whole blood is stirred by repeating suction and discharge with the use of the pipetting tip, and is then sucked in a definite amount followed by discharge into first mixing cell 14 and second mixing cell 16. To stir the diluted specimen, suction and discharge with the pipetting tip are repeated.

Before sucking liquid reagent A with the pipetting tip, the first washing is carried out by using the remaining liquid diluent in liquid diluent cell 13. This washing is performed by repeatedly sucking and discharging the remaining liquid diluent several times. After washing, liquid reagent A is sucked in a definite amount and is discharged into first mixing cell 14. Then, liquid reagent A is allowed to react with the diluted specimen under stirring by repeating suction and discharge with the pipetting tip several times.

Next, the second washing of the pipetting tip is effected by repeatedly sucking and discharging liquid reagent A remaining in first liquid reagent cell 15. Then, liquid reagent B contained in second liquid reagent cell 17 is sucked in a definite amount and is discharged into second mixing cell 16. Liquid reagent B is allowed to react with the diluted specimen under stirring by repeating suction and discharge several times.

Thus, the pipetting tip is washed with the liquid for diluting the specimen the first time and then with remaining liquid reagent A the second time. When liquid reagent A somewhat affects the reaction with liquid reagent B, it is recommended that the reaction in second mixing cell 16 is first performed by collecting liquid reagent B, subsequently the pipetting tip is washed with remaining liquid reagent B, and then liquid reagent A is sucked and reacted in first mixing cell 14. By selecting a liquid, which exerts no effect on the reaction, for washing among the remaining liquids as in the above case, the assay data become more reliable.

It is necessary to preliminarily examine how much the liquid reagent to be used as the washing liquor affects the subsequent reaction. Then, the order of using the remaining liquid reagents can be determined.

In Examples 1 and 3, two liquid reagents, two liquid reagent cells, and two mixing cells are used, but each of them may be one, or three or more.

This application is based on Japanese application No. 2000-134478, filed on May 8, 2000, the entire content of which is incorporated herein by reference.

While the invention has been described in detail and with reference to specific embodiments thereof, it will be apparent to one skilled in the art that various changes and modifications can be made therein without departing from the spirit and scope thereof. All references cited herein are incorporated, by reference, in their entirety.

What is claimed is:

1. A method of assaying a specimen, comprising:
preparing (i) a specimen, (ii) a liquid cell in which a liquid used for assaying a component in the specimen is to be contained, and (iii) a mixing cell wherein the specimen and the liquid are mixed;
supplying a liquid reagent into the liquid cell in an amount exceeding the amount required in the assay;
pipetting a portion of the specimen and a portion of the liquid into the mixing cell using a pipetting tip; and
washing the pipetting tip with the liquid remaining in the liquid cell, wherein the pipetting tip is disposed within the liquid cell.

2. The method according to claim 1, wherein the liquid used for assaying a component in the specimen is at least one selected from the group consisting of a liquid reagent and a liquid diluent.

3. The method according to claim 1, wherein the inside of the pipetting tip is pre-washed with said liquid contained in the liquid cell before said step of pipetting a portion of the specimen into the mixing cell.

4. The method according to claim 1, wherein the step of washing the pipetting tip with the liquid remaining in the liquid cell is performed after said step of pipetting a portion of the liquid or a portion of the specimen into the mixing cell.

5. The method according to claim 1, wherein
the step of pipetting a portion of the liquid into the mixing cell using a pipetting tip is performed; and then
the step of pipetting a portion of the specimen into the mixing cell using the pipetting tip is performed; and then
the step of washing the pipetting tip with the liquid remaining in the liquid cell is performed.

6. The method according to claim 1, wherein
the step of pipetting a portion of the specimen into the mixing cell using a pipetting tip is performed; and then
the step of pipetting a portion of the liquid into the mixing cell using the pipetting tip is performed; and then
the step of washing the pipetting tip with the liquid remaining in the liquid cell is performed.

7. The method according to claim 1, wherein said step of pipetting the portion into the mixing cell includes a step of sucking the portion and discharging the sucked portion into the mixing cell.

8. The method according to claim 1, wherein said step of pipetting a portion of the specimen and a portion of the liquid into the mixing cell is performed by using the same pipetting tip.

9. A method of assaying a specimen, comprising:
preparing (i) a specimen, (ii) a liquid reagent cell in which a liquid reagent is to be contained and a liquid diluent in which a liquid diluent is to be contained, and (iii) a mixing cell wherein the specimen and the liquid reagent are mixed;
supplying a liquid reagent and a liquid diluent respectively into the liquid reagent cell and the liquid diluent in respective amounts each exceeding the amount required in the assay; and
pipetting a portion of the specimen, a portion of the liquid reagent and a portion of the liquid diluent into the mixing cell using a pipetting tip; and
said method further comprising at least one step of:
washing the pipetting tip with the liquid remaining in the liquid reagent cell, wherein the pipetting tip is disposed within the liquid reagent cell, and washing the pipetting tip with the liquid remaining in the liquid diluent cell, wherein the pipetting tip is disposed within the liquid diluent cell.

10. The method according to claim 9, wherein the inside of the pipetting tip is pre-washed with the liquid contained in the liquid reagent cell before said step of pipetting a portion of the specimen into the mixing cell.

11. The method according to claim 9, wherein the inside of the pipetting tip is pre-washed with said liquid contained in the liquid diluent cell before said step of pipetting a portion of the specimen into the mixing cell.

12. The method according to claim 9, wherein the step of washing the pipetting tip with the liquid remaining in the liquid reagent cell is performed after said step of pipetting a portion of the liquid reagent, a portion of the liquid diluent or a portion of the specimen into the mixing cell.

13. The method according to claim 9, wherein the step of washing the pipetting tip with the liquid remaining in the liquid diluent cell is performed after said step of pipetting a portion of the liquid reagent, a portion of the liquid diluent or a portion of the specimen into the mixing cell.

14. The method according to claim 9, wherein
the step of pipetting a portion of the liquid diluent into the mixing cell using a pipetting tip is performed; and then
the step of pipetting a portion of the specimen into the mixing cell using the pipetting tip is performed; and then
the step of washing the pipetting tip with the liquid remaining in the liquid diluent cell is performed; and then
the step of pipetting and a portion of the liquid reagent into the mixing cell using the pipetting tip is performed.

15. The method according to claim 9, wherein
the step of pipetting a portion of the liquid reagent into the mixing cell using a pipetting tip is performed; and then
the step of pipetting a portion of the specimen into the mixing cell using the pipetting tip is performed; and then
the step of washing the pipetting tip with the liquid remaining in the liquid reagent cell is performed; and then
the step of pipetting and a portion of the liquid diluent into the mixing cell using the pipetting tip is performed.

16. The method according to claim 9, wherein
the step of pipetting a portion of the liquid reagent and a portion of the liquid diluent into the mixing cell using a pipetting tip is performed; and then
the step of pipetting a portion of the specimen into the mixing cell using the pipetting tip is performed; and then
the step of washing the pipetting tip with the liquid remaining in the liquid reagent cell is performed.

17. The method according to claim 9, wherein
the step of pipetting a portion of the liquid reagent and a portion of the liquid diluent into the mixing cell using a pipetting tip is performed; and then
the step of pipetting a portion of the specimen into the mixing cell using the pipetting tip is performed; and then
the step of washing the pipetting tip with the liquid remaining in the liquid diluent cell is performed.

18. The method according to claim 9, wherein said step of pipetting the portion into the mixing cell includes a step of sucking the portion and discharging the sucked portion into the mixing cell.

19. The method according to claim 9, wherein said step of pipetting a portion of the specimen, a portion of the liquid reagent and a portion of the liquid diluent into the mixing cell is performed by using the same pipetting tip.

20. A method of assaying a specimen, comprising:
preparing (i) a specimen, (ii) a first liquid reagent cell in which a first liquid reagent is to be contained, and a second liquid reagent cell in which a second liquid reagent is to be contained, and (iii) a first mixing cell wherein the specimen and the first liquid reagent are mixed, and a second mixing cell wherein the specimen and the second liquid reagent are mixed;
supplying a first liquid reagent and a second liquid reagent respectively into the first liquid reagent cell and the second liquid reagent cell in respective amounts each exceeding the amount required in the assay;
pipetting a portion of the first liquid reagent into the first mixing cell using a pipetting tip;
pipetting a portion of the second liquid reagent into the second mixing cell using the pipetting tip;
pipetting a portion of the specimen into the first mixing cell using the pipetting tip;
washing the pipetting tip with the liquid remaining in the second liquid reagent cell; wherein the pipetting tip is disposed within the second liquid reagent cell; and
pipetting a second portion of the specimen into the second mixing cell using the pipetting tip.

21. The method according to claim 20, wherein said step of pipetting the portion into the mixing cell includes a step of sucking the portion and discharging the sucked portion into the mixing cell.

22. A method of assaying a specimen, comprising:
preparing (i) a specimen, (ii) a first liquid reagent cell in which a first liquid reagent is to be contained, a second liquid reagent cell in which a second liquid reagent is to be contained and a liquid diluent cell in which a liquid diluent is to be contained, and (iii) a first mixing cell wherein the specimen and the first liquid reagent are mixed, and a second mixing cell wherein the specimen reacts with the second liquid reagent;
supplying a first liquid reagent, a second liquid reagent, and a liquid diluent respectively into the first liquid reagent cell, the second liquid reagent cell, and the liquid diluent cell in respective amounts each exceeding the amount required in the assay;
pipetting a portion of the liquid diluent into the first mixing cell and the second mixing cell using the pipetting tip;
pipetting a portion of the specimen into the first mixing cell and the using the pipetting tip;
pipetting a second portion of the specimen into the second mixing cell using the pipetting tip;
washing the pipetting tip with the liquid remaining in the liquid diluent cell, wherein the pipetting tip is disposed within the liquid diluent cell;
pipetting a portion of the first liquid reagent into the first mixing cell using a pipetting tip;
washing the pipetting tip with the liquid remaining in the first liquid reagent cell wherein the pipetting tip is disposed within the first liquid reagent cell; and
pipetting a portion of the second liquid reagent into the second mixing cell using the pipetting tip.

23. The method according to claim 22, wherein said step of pipetting the portion into the mixing cell includes a step of sucking the portion and discharging the sucked portion into the mixing cell.

* * * * *